United States Patent [19]
Conner et al.

[11] Patent Number: 6,105,441
[45] Date of Patent: Aug. 22, 2000

[54] PRODUCT SAMPLER SYSTEM AND METHOD

[75] Inventors: David B. Conner, Kilgore; Antonio M. Mendez; Greg T. Slemons, both of Longview; Calvin W. Whiddon, Beckville, all of Tex.

[73] Assignee: Eastman Chemical Company, Kingsport, Tenn.

[21] Appl. No.: 09/238,470

[22] Filed: Jan. 28, 1999

[51] Int. Cl.[7] .................................................. G01N 1/00
[52] U.S. Cl. ........................................................ 73/863.86
[58] Field of Search .................. 73/863, 863.81–863.83, 73/863.85, 863.86, 864, 864.3, 864.33, 864.73, 864.74, 864.91, 865.8, 865.9

[56] References Cited

U.S. PATENT DOCUMENTS

| | | | |
|---|---|---|---|
| 3,383,923 | 5/1968 | Conche et al. | 73/421 |
| 3,991,627 | 11/1976 | Laird et al. | 73/864.91 |
| 4,118,987 | 10/1978 | Zeh | 73/422 |
| 4,174,632 | 11/1979 | Jansen | 73/422 |
| 4,643,027 | 2/1987 | Deutsch et al. | 73/865.8 |
| 4,651,574 | 3/1987 | Spencer | 73/864.74 |
| 4,887,472 | 12/1989 | Jansen | 73/863.86 |
| 4,989,463 | 2/1991 | Cimaglia et al. | 73/863.86 |
| 5,301,500 | 4/1994 | Hines | 60/39.161 |
| 5,351,859 | 10/1994 | Jansen | 222/82 |
| 5,361,643 | 11/1994 | Boyd et al. | 73/863.71 |
| 5,431,067 | 7/1995 | Anderson et al. | 73/863.86 |
| 5,594,182 | 1/1997 | Jansen | 73/863.71 |

FOREIGN PATENT DOCUMENTS

549706 6/1977 U.S.S.R. .

*Primary Examiner*—Robert Raevis
*Attorney, Agent, or Firm*—Matthew W. Smith; Harry J. Gwinnell

[57] ABSTRACT

A sampler assembly and a method of collecting a sample of a process are disclosed. The sampler assembly includes a lid subassembly and a housing body subassembly. The housing body subassembly includes a housing body that accommodates different sizes and shapes of collection bottles. The housing body includes lateral and axial adjustment devices with bottle engaging pads with surfaces that contact and support the collection bottle. The adjustment devices may be either manually or automatically adjusting components, and may be adjusted for any type of collection bottle. The lid subassembly includes a lid, a bracket coupled to the lid for supporting the sampler assembly, a plug disposed in the lid, a supply line and a vent line. The housing body subassembly includes a housing body releasable coupled to the lid, lateral and axial adjustment devices, and a shield to protect the operator.

15 Claims, 12 Drawing Sheets

PRODUCT SAMPLER SYSTEM AND METHOD

BACKGROUND OF THE INVENTION

1. Field of the Invention

The present invention relates generally to devices for sampling chemical processes, and more particularly to a sampling device that readily permits collection of samples of varying size.

2. Description of the Related Art

It is typical in industrial processes to periodically sample the materials contained in, or conducted through, various parts of the process. The materials may be gases, liquids, slurries, or solutions, and the samples may be used for lab retention, product evaluation, or process analysis. Depending on the sampling requirement, the amount of sampled material needed can vary. The materials are often noxious or hazardous, and at the point of sampling may be under high pressure or at high temperatures. The design of a sampling device or technique should therefore address varying sample volume requirements and the prevention of inadvertent release of the sampled material from the process to protect the personnel taking the sample as well as other personnel, or the environment. It is also helpful for personnel taking a sample to be able to visually monitor the progress of the sampling to verify that the desired amount of sampled material is collected. Further, sampling devices are subject to wear or damage, and may be needed to be added or removed at various times to various points in the sampled process. It is therefore also desirable for sampling devices to be amenable to ready repair or replacement of parts, and to be easily installed and removed. A variety of sampling devices and techniques have been developed which do not satisfactorily address these needs.

A known liquid sampler is disclosed in U.S. Pat. No. 4,174,632 to Jansen ("Jansen '632"). The disclosed sampling device includes a branch line 3 fixed to a process line 1. A valve 4 is fixed to the branch line and includes a cap 6 surrounding an injection needle 9 and a desaeration needle 11. A sample flask 7 has a septum 8 in its opening. The interior profile of the cap is matched to the exterior profile of the sample flask. To take a sample from the process line, the sample flask is inserted into the cap so that the injection needle pierces the septum. The valve is opened, allowing the material in the process line to flow through the branch line, valve, and injection needle into the sample flask. When the desired amount of material is collected (monitored through a slot 10 formed in the side of the cap), the valve is closed, and the bottle withdrawn from the cap. The Jansen '632 device provides for only a single size of sample container. The entire sampler is suspended from the branch line, relying on the branch line's connection to the process line for support. The constituent parts of the sampler are not readily replaceable (for example, the injection and desaeration needles are fixed in the upper end of the cap). Further, the personnel taking the sample are potentially exposed to the sampled material, via the slot in the cap, if the sample flask ruptures.

Another known sampler is disclosed in U.S. Pat. No. 4,887,472 to Jansen ("Jansen '472"). The disclosed sampler includes a valve 1 (which communicates with the process to be sampled), a hood 2 coupled to the valve, a sleeve 3 mounted for reciprocal movement within the hood, and a bottle retainer 4 mounted for reciprocal movement about the exterior of the hood. Process needle 6 is mounted in the hood. A sample bottle 27 with septum 26 in its opening can be disposed within the bottle retainer 4, which includes a slit to enable the sample bottle to be viewed during filling. The Jansen '472 device also does not accommodate sample bottles of differing size, and similarly exposes the sampling personnel via the slit in the bottle retainer.

Soviet Union Patent Publication No. 549,706 discloses another sampler which appears to have a cap 14 mounted to a valve for reciprocal movement with respect to a fixed injection needle 11, and a bottle retainer 15 mountable to the cap to enclose a sample bottle 17. The bottle retainer 15 also appears to have a viewing slit 16. This sampler thus suffers from the same shortcomings as Jansen '472 and Jansen '632.

SUMMARY OF THE INVENTION

The shortcomings of the prior art are overcome by the sampler assembly of the present invention, which provides a sampler assembly that can accommodate and support different sizes and shapes of collection bottles. To collect a sample, an operator opens a valve on a supply line to the sampler assembly, thereby allowing a process to flow to the sampler assembly. The sampler assembly includes a housing body that surrounds a collection bottle. The housing body includes openings through which the operator can watch the level of the sample in the collection bottle. A shield is provided around a portion of the housing body to protect the operator from any spray of the sample. When the collected sample reaches a desired level, the operator may close the valve and remove the housing body to access the collection bottle. The collection bottle may be decoupled from the sampler assembly and analyzed or tested.

The sampler assembly includes lateral and axial adjustment devices that are used to contact and support different sized collection bottles in the housing body. There are several embodiments of adjustment devices that effectively support a collection bottle. One embodiment includes adjustment devices having a surface or bottle engaging pad that contacts a surface of a collection bottle. The position of the pad may be adjusted with respect to the housing body. Another embodiment includes adjustment devices with contact surfaces that are moved into contact with a collection bottle when a portion of the housing body is rotated. The adjustment devices eliminate the need to-replace the housing body in order to accommodate collection bottles of different sizes, thereby simplifying the collection of different amounts of samples.

The sampler assembly also includes a mounting bracket for supporting the sampler assembly. The bracket may be secured to a lid to mount the assembly at any desired location. The sampler assembly also includes a plug connected to the lid. The plug includes holes for a sample needle and a vent needle. The collection bottle is mounted on the needles. Finally, the sampler assembly can be disassembled for easy maintenance and part replacement.

DETAILED DESCRIPTION OF THE INVENTION

A sampler system and method embodying the principles of the invention is first illustrated and described schematically and in summary form below. A more detailed illustration and descriptions of the preferred embodiments are then presented.

Figure 1:
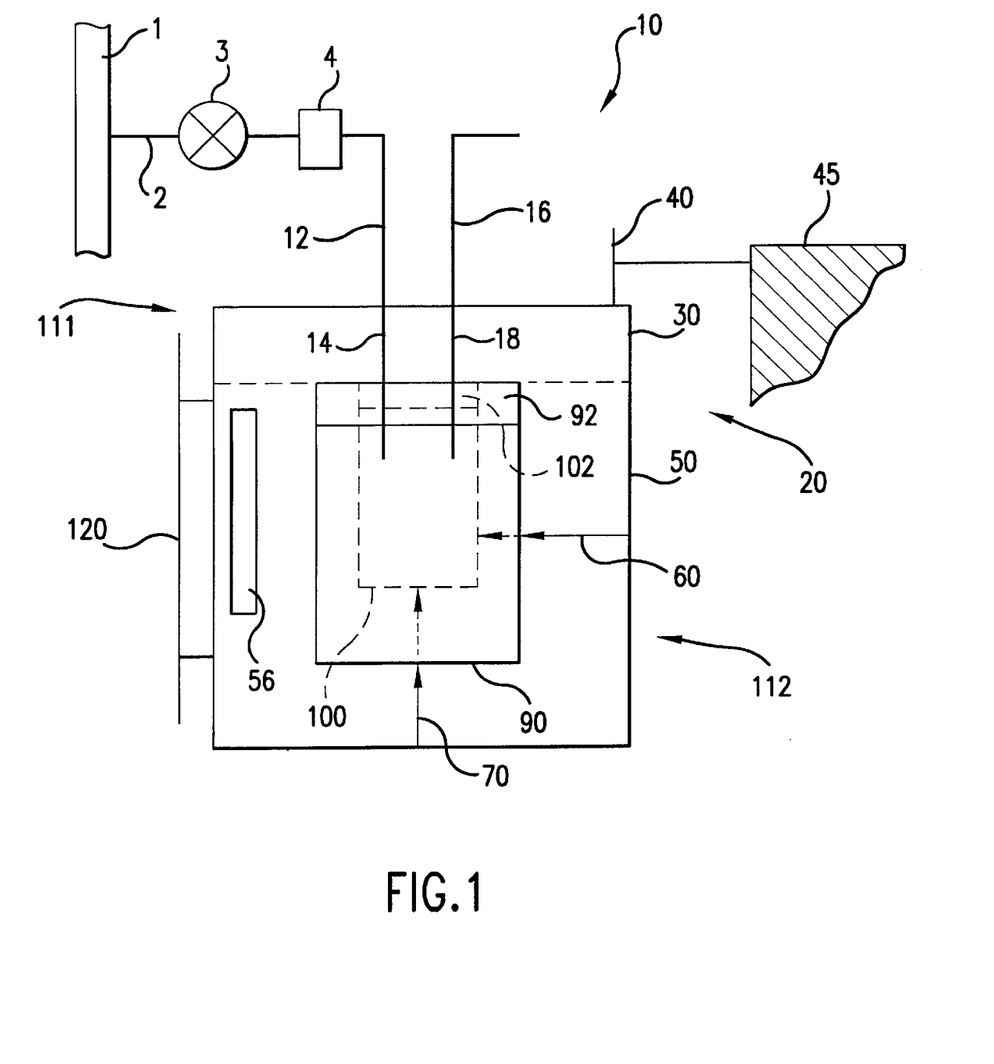
FIG. 1 is a schematic illustration of a sampling system embodying the principles of the invention.

FIG. 1 schematically illustrates a sampler system. A process from which a sample of material is to be extracted is illustrated schematically as a pipeline 1. The material may be a gas, liquid, or slurry. A tap line 2 is coupled to pipeline 1 to provide access to the material in the pipeline 1. A valve 3 is disposed on tap line 2 to selectively allow material to flow from pipeline 1 through tap line 2. Optionally, a filter 4 may be placed in tap line 2 to filter the material. A sampler assembly 10 is coupled to tap line 2.

Sampler assembly 10 includes a collection bottle housing 20 with a housing body 50 and a lid 30 coupleable to the housing body 50. A supply line 12, fluidically coupled to tap line 2, passes through the lid 30, and terminates in a supply needle 14. Similarly, a vent line 16 passes through the lid 30 and has a vent needle 18 at one end, the other end communicating with the ambient environment. Housing 20 is supported on any suitable supporting structure 45 (which may be pipeline 1, a nearby wall, ceiling, etc.) by a mounting bracket 40. Housing body 50 can include an opening 56 through which the interior of the housing 20 can be viewed. A shield 120 can be disposed adjacent the opening 56 to protect an operator from any material that may be ejected from the housing through opening 56.

Collection bottles 90; 100, of different sizes and capacities, and of conventional construction, can be used with the sampler assembly to collect samples of different sizes. Collection bottles 90, 100, have septums 92, 102, respectively, closing their open ends. The bottles 90, 100, can be placed in housing 20 (bottle 100 is shown in phantom in FIG. 1) with supply and vent needles 14, 18, piercing their septums 92, 102, respectively. A lateral adjustment device 60 mounted in housing 20 is adjustable to contact the sides of the collection bottles 90, 100, to fix their position in the housing 20. Similarly, an axial adjustment device 70 mounted in housing 20 is adjustable to engage the lower end of a selected collection bottle to support the bottle in an operative position on the needles 14, 18.

The sampler assembly 10 can be operated as follows when it is desired to secure a sample from pipeline 1. The size of the sample to be taken is first determined. A collection bottle appropriate for the desired sample size is selected. The selected collection bottle is fixed onto the supply and vent needles 14, 18, by piercing its septum. The housing body 50 is then coupled to the lid 30, enclosing the collection bottle. Axial adjustment device 70 and lateral adjustment device 60 are adjusted to securely support the collection bottle in its operative position. Valve 3 is then opened, allowing material to flow through tap line 2 (and optionally filter 4), supply line 12, supply needle 14, and into the collection bottle. Air displaced from the sample bottle by the sampled materials is released through vent needle 18 and vent line 16 The operator views the bottle through shield 120 and opening 56, and closes the valve 3 when the material reaches an appropriate level in the collection bottle.

Two preferred embodiments of the sampler assembly 10 are described in more detail below, using the same reference numbers as used above in the schematic description of the invention. The first preferred embodiment is shown in FIGS. 2A through 11B.

In the first preferred embodiment, sampler assembly 10 includes two major subassemblies: a) a lid subassembly 111 coupled to the supply line 12 and to supporting structure 45; and b) a housing body subassembly 112 coupled to lid subassembly 111. Lid subassembly 111 includes: bracket 40; lid 30 coupled to, and supported by, bracket 40; plug 80 disposed in lid 30; and supply line 12 and vent line 16 disposed in plug 80. Housing body subassembly 112 includes: housing body 50 releasably coupleable to lid 30; lateral adjustment device 60; axial adjustment device 70; and shield 120.

Sampler assembly 10 is useable with collection bottles, such as containers 90 and 100 identified above, of various sizes, dimensions, and structures. In the embodiment illustrated below, the structure and operation of sampler assembly 10 is illustrated with collection bottle 90, which is generally cylindrical and has an open end sealed by septum 92. Collection bottle 90 is glass, while septum 92 is polytetrafluoroethylene (PTFE).

Figure 2A:
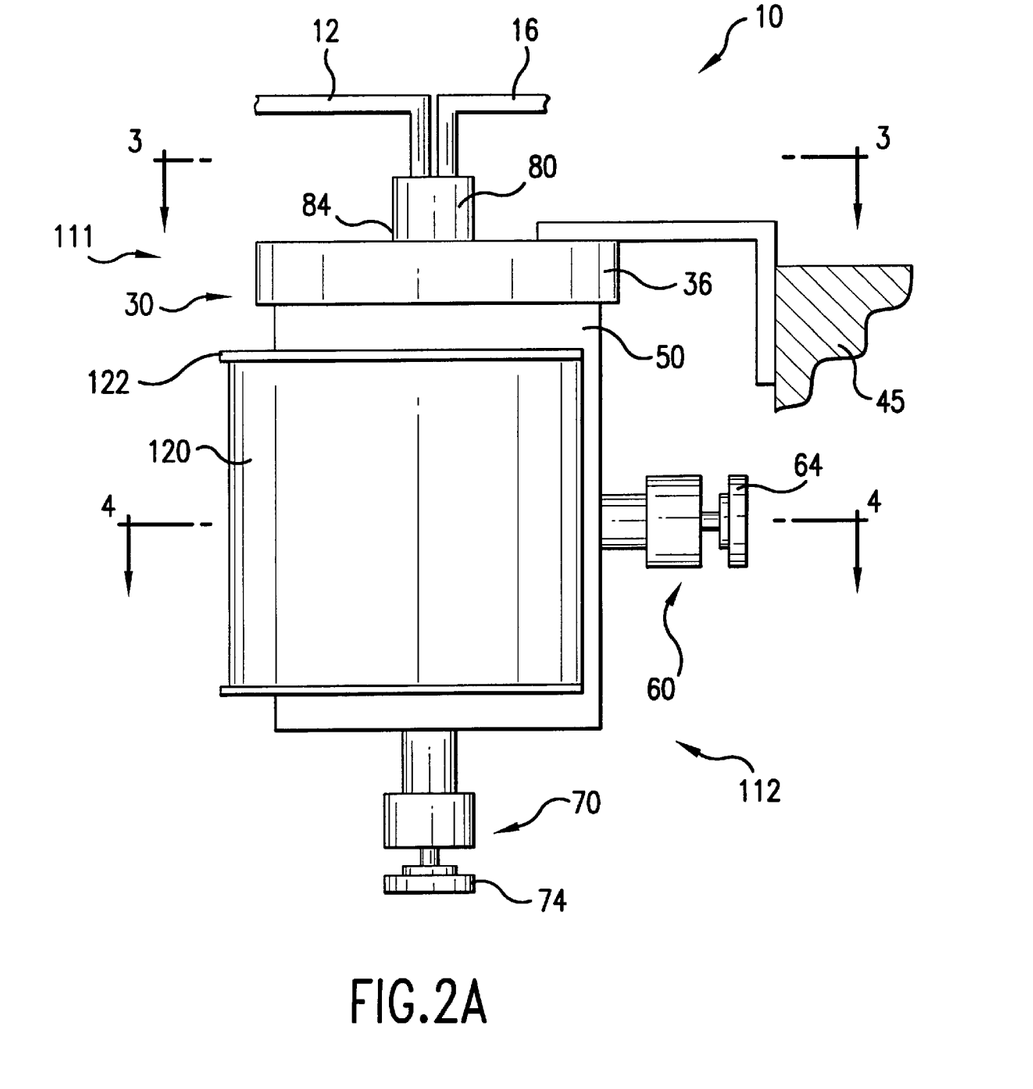
FIGS. 2A–2B are a side view and an exploded side view of a first embodiment of a sampler assembly.
Figure 2B:
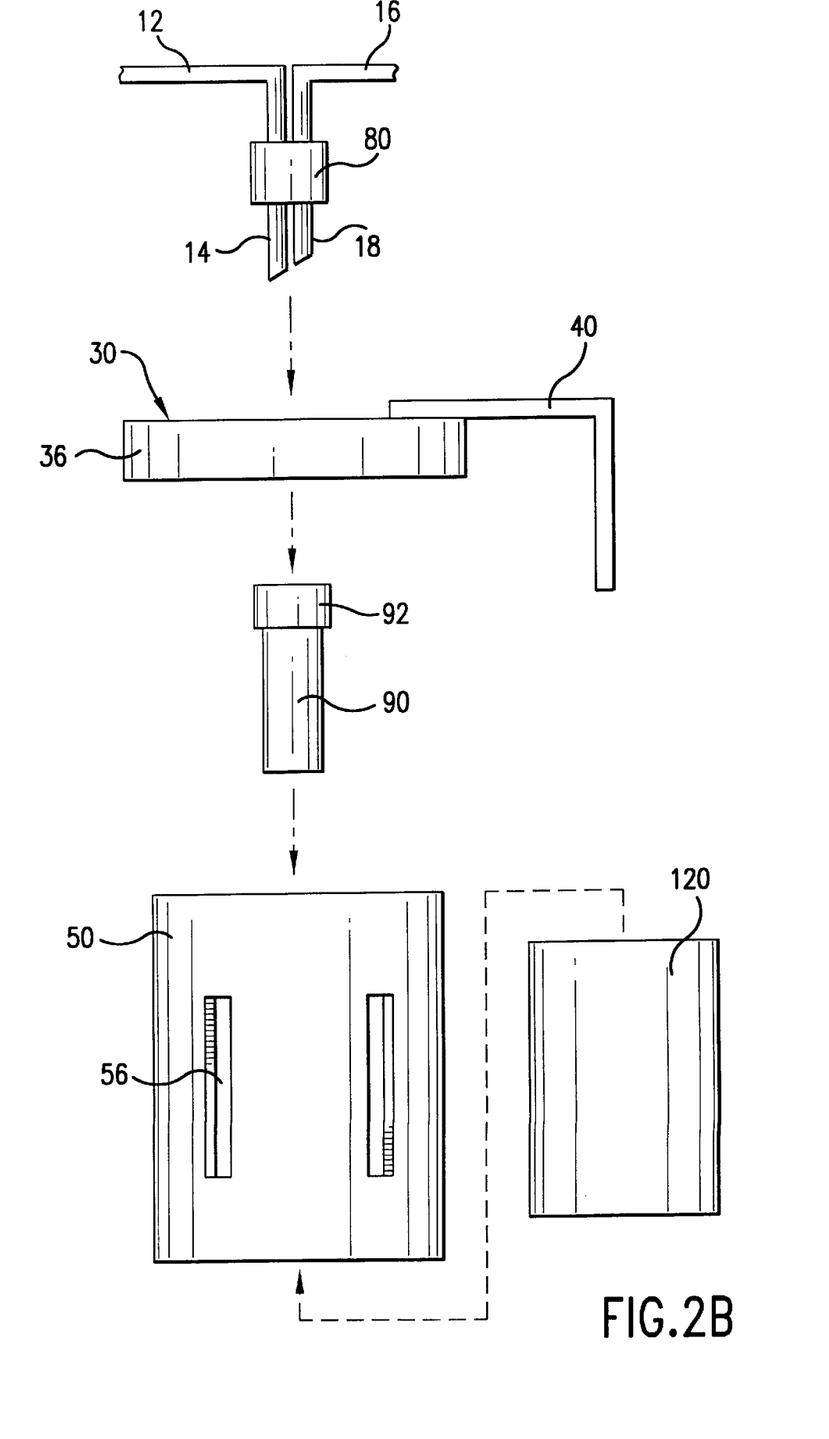

As shown in FIGS. 2A–2B, the lid subassembly 111 includes a bracket 40 connected to a supporting structure 45 and supporting the sampler assembly 10. Preferably, bracket 40 is connected to supporting structure 45 by bolts (not shown) through holes (not shown) in the bracket 40. The bracket 40 is coupled to lid 30 by a welded connection and may be connected at any location on the lid 30. Bracket 40 allows the sampler assembly 10 to be mounted in any number of locations. Preferably, the bracket 40 is made of stainless steel.

Figure 6A:
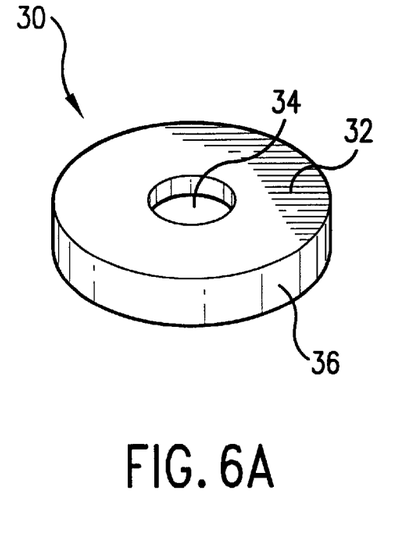
FIGS. 6A–6C are perspective, top, and cross-sectional views of the lid of the sampler assembly of FIGS. 2A–B.
Figure 6B:
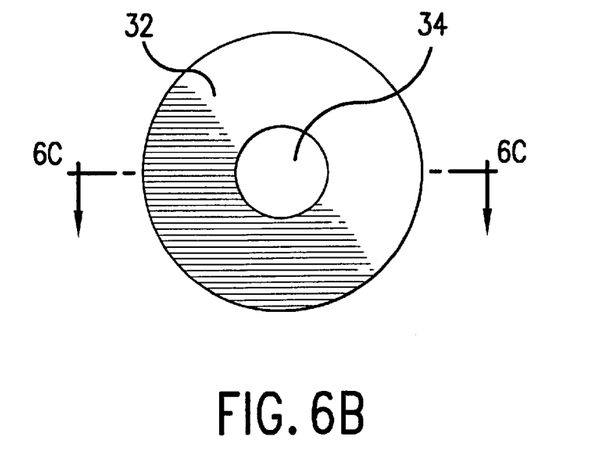
Figure 6C:
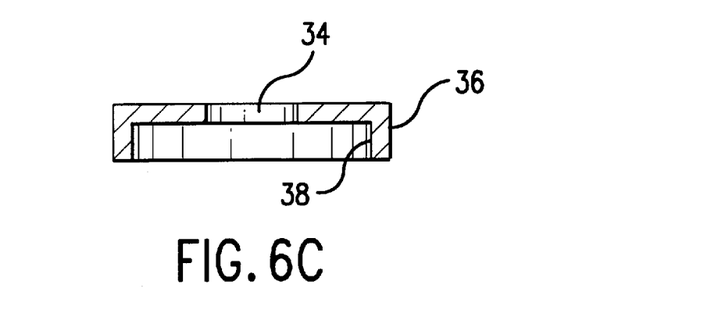
Figure 7A:
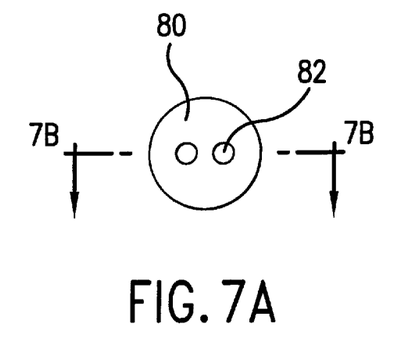
FIGS. 7A–7B are top and cross-sectional views of the plug of the sampler assembly of FIGS. 2A–B.
Figure 7B:
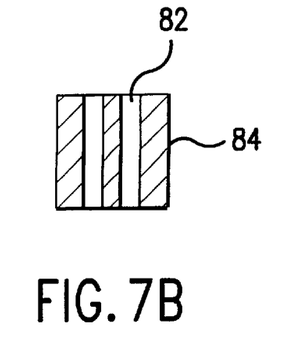
Figure 8:
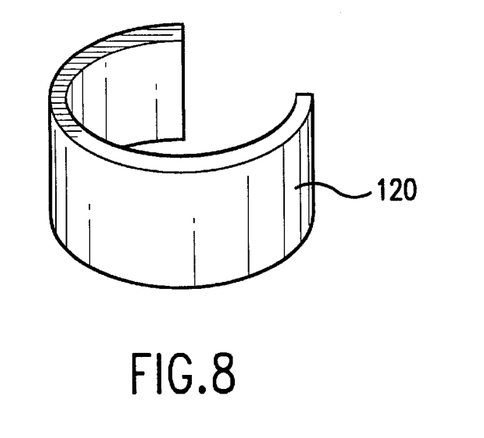
FIG. 8 is a perspective view of the shield of the sampler assembly of FIGS. 2A–B.

The lid subassembly 111 also includes a plug 80 that facilitates the communication of the supply line 12 and vent line 16 to the interior of the collection bottle housing 20. Plug 80 is removably connected to lid 30 to simplify the assembly of the sampler assembly 10. Plug 80 includes an outer surface 84 which is threaded. As shown in FIGS. 6A–6C, lid 30 includes a body portion 32 defining an opening 34 that facilitates the connection with plug 80. The inner surface of opening 34 is also threaded. Accordingly, plug 80 is threaded into hole 34 to couple the plug 80 and the lid 30.

As discussed previously, supply line 12 and vent line 16 include needles 14 and 18, respectively, to communicate with the interior of housing 20. Plug 80 includes two holes 82 through which needles 14 and 18 are inserted. (See FIG. 5.) The needles 14 and 18 are inserted into the holes 82 until they extend beyond the bottom surface of the plug 80.

Turning to the other subassembly of the sampler assembly 10, housing body subassembly 112 includes a housing body 50 releasably coupleable to lid 30. Housing body 50 is sized to hold a variety of shapes and sizes of collection bottles. When housing body 50 is coupled to lid 30, needles 14 and 18 are in communication with the interior of housing body 50.

Figure 5:
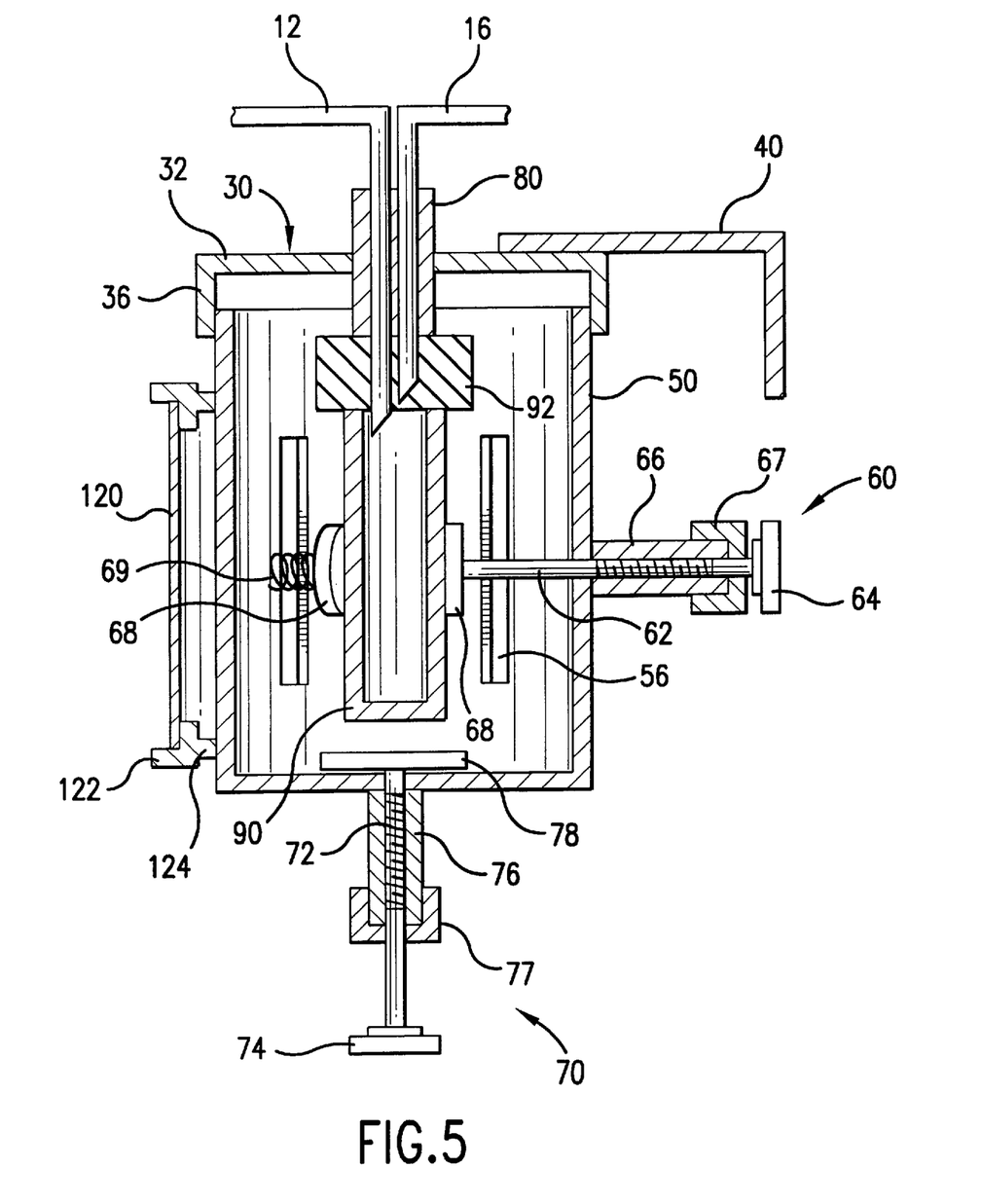
FIG. 5 is a cross-sectional view of the sampler assembly along the line "5—5" in FIG. 3.

Different sizes and shapes of collection bottles can be supported in the housing body 50. As shown in FIG. 5, a lateral adjustment device 60 and an axial adjustment device 70 are coupled to housing body 50 and are used to provide support to a collection bottle in a lateral direction and axial direction, respectively. Lateral adjustment device 60 and axial adjustment device 70 ensure that a collection bottle remains in communication with the supply line 12 even if the sample being taken is at an extremely high pressure and high temperature.

The housing body subassembly 112 includes a shield 120 to protect the operator as the level of the sample is viewed. The shield 120 is coupled to housing body 50 and is transparent to allow the operator to view the interior of the housing body 50 through the openings 56. The shield 120 provides protection to the operator from a potential spray of sample through the openings 56.

Turning to the connection between the lid 30 and the housing body 50, the connection is shown in FIG. 5 and the lid 30 components are shown in FIGS. 6A–6C. As discussed previously, the housing body 50 is easily coupleable to the lid 30 to permit access to the inside of the housing body 50. Once bracket 40 is secured to a supporting structure 45, the housing body 50 can be readily connected to and removed from the lid 30.

In the first preferred embodiment, the external circumferential surface of the housing body 50 near the top of the body is threaded. As shown in FIG. 6C, the lid 30 has a side portion 36 with a threaded inner surface 38 that corresponds to the threads on the housing body 50. The threaded connection between the housing body 50 and the lid 30 makes them easily coupleable. Preferably, lid 30 and housing body 50 are made from stainless steel.

As discussed above, the lateral adjustment device 60 contacts a side of the collection container 90 inside the housing body 50. The use of lateral and axial adjustment devices allows sample bottles of differing sizes to be securely positioned and supported within the housing body 50. Several embodiments of a lateral adjustment device 60 according to the invention are disclosed.

Figure 4:
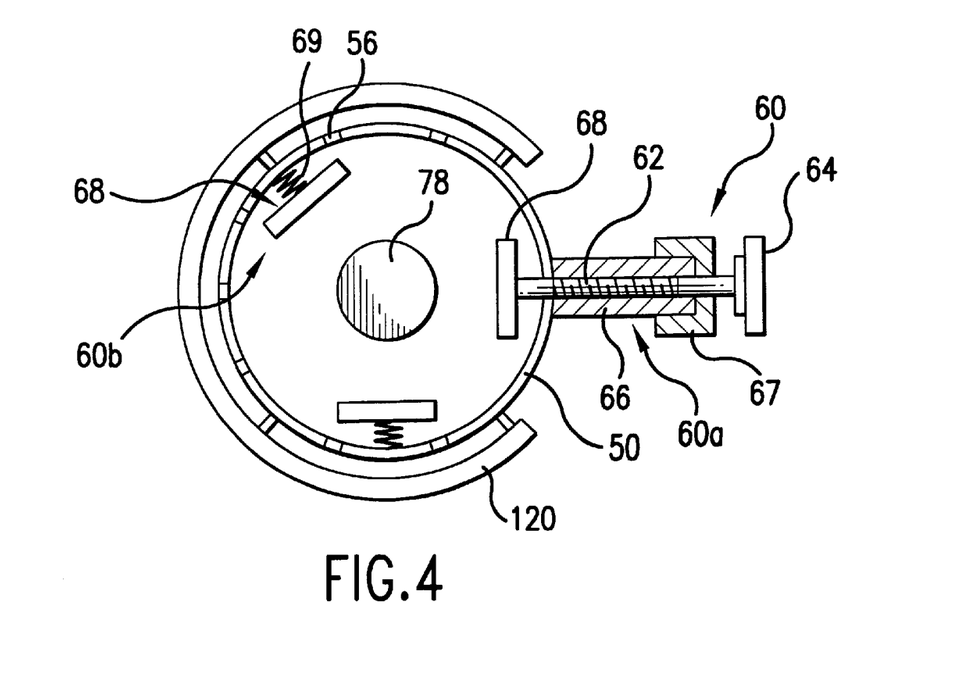
FIG. 4 is a cross-sectional view of the sampler assembly along the line "4—4" in FIG. 2A.

The embodiment of lateral adjustment device 60 shown in FIGS. 4 and 5 includes manually adjusting components 60a and automatically adjusting components 60b. Manually adjusting component 60a includes, an externally-threaded rod 62 with an adjustment knob 64 attached at one end and a bottle engaging pad 68 attached at the other end. Rod 62 is mounted in tube 66, which has a mating internal thread. The tube 66 is welded to the outer surface of housing body 50. The pad 68 is moved to a particular location by rotating the adjustment knob 64 which moves rod 62 along the threads of the tube 66. A sleeve 67 is provided on the end of tube 66. For a collection bottle with a small width, pad 68 may be moved inwardly so that a bottle engaging surface thereon contacts a side of the collection bottle. The reverse is true for a collection bottle with a large width. Pad 68 may be moved to a particular position and will remain in that position until further adjustments are made.

Since collection bottles may have different shapes, pad 68 and rod 62 may be rigidly connected or pivotably connected. A pivoting connection would allow the pad 68 to contact and support collection bottles with numerous different shapes.

Manually adjusting component 60a is welded perpendicularly to housing body 50. However, in order to accommodate different shaped collection bottles, manually adjusting component 60a may be mounted on housing body 50 at an orientation other than perpendicular to the outer surface. Manually adjusting component 60a may also be connected to housing body 50 with any other type of connection which will support the adjustment device.

Referring to FIGS. 4–5 and 11A–B, lateral adjustment device 60 also includes automatically adjusting components 60b which include a spring 69 and a pad 68. The spring 69 biases the pad 68 so that a bottle engaging surface thereon is in constant contact with a surface of a collection bottle 90 and provides support thereto. One end of spring 69 is welded to the inner surface of the housing body 50 and the other end is welded to a surface of pad 68. Accordingly, in its normal operating state, the spring 69 biases the pad 68 toward the center of the housing body 50. Spring 69 may be compressed to accommodate a collection bottle 90 with a large width.

While welded connections are preferred between the pad, spring, and housing body, any connection that permits the adjustment device to support a collection bottle may be used. The pad 68 is preferably formed of polytetrafluoroethylene (PTFE) so that it will not scratch the surface of the collection bottle 90.

Lateral adjustment device 60 can include various combinations of manually adjusting components 60a and automatically adjusting components 60b are provided at different locations on the housing body 50 to support and stabilize a collection bottle 90. A preferred embodiment of the invention, shown in FIGS. 4 and 5, contemplates the use of two components 60b and one component 60a spaced 120 degrees apart along the inside the housing body 50. It is noted that any combination and number of manually and automatically adjusting components 60a and 60b may mounted to the housing body 50 so long as the collection bottle 90 is laterally supported.

A collection bottle 90 must be supported from below as well. Accordingly, the housing body subassembly 112 includes an axial adjustment device 70 that is connected to the bottom surface of the housing body 50. Similar to the manually adjusting component 60a, the axial adjustment device 70 includes a pad 78 that is moveable to a particular location and remains in that location until an operator or machine move it. The axial adjustment device 70, shown in FIG. 5, has a rod 72, an adjustment knob 74, a tube 76, a sleeve 77, and a pad 78 with a bottle engaging surface. Each of these parts corresponds to a part discussed above for the manually adjusting component 60a. It is noted that while the axial adjustment device 70 may be an automatically adjusting component, such a device would not hold a pad in a fixed location.

The purpose of each adjustment device is to provide support to a surface of a collection bottle. In the first preferred embodiment, a threaded connection is used in each manually adjusting component to convert the rotation of the knob into linear movement of the pad. It is noted that any other connection that would advance the pad may be used between the rod and the tube in an adjustment device.

The sampler assembly 10 includes a collection bottle 90 to collect the sample. The collection bottle 90 is sized so that it fits inside the housing body 50, as shown in FIGS. 2A–2B. As discussed previously, the collection bottle 90 includes a septum 92 on its open end. Once the housing 50 is disconnected from lid 30, the end of the collection bottle 90 with the septum 92 is slid onto needles 14 and 18 (see FIG. 5). The collection bottle 90 is pushed upwardly so that its septum 92 is pierced by needle portions 14 and 18 and is pushed until the top surface of the septum 92 contacts the bottom surface of the plug 80. When the collection bottle 90 is in its operative position, the needle 14 of the supply line 12 is in fluidic communication with the interior of the collection bottle 90.

Figure 9:
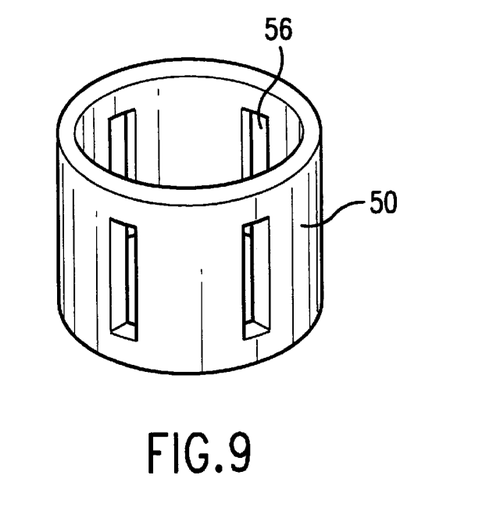
FIG. 9 is a perspective view of the housing body of the sampler assembly of FIGS. 2A–B.
Figure 10:
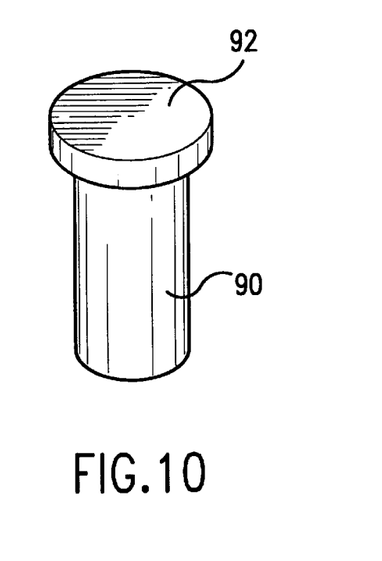
FIG. 10 is a perspective view of a collection bottle used in the sampler assembly of FIGS. 2A–B.
Figure 11A:
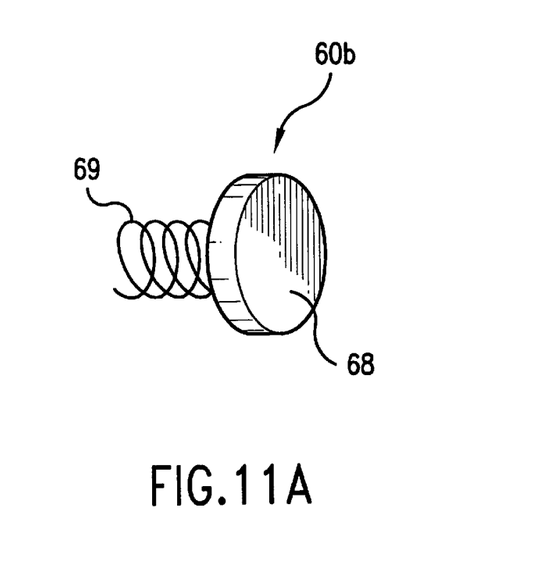
FIGS. 11A–11B are perspective and top views of an adjustment device of the sampler assembly of FIGS. 2A–B.
Figure 11B:
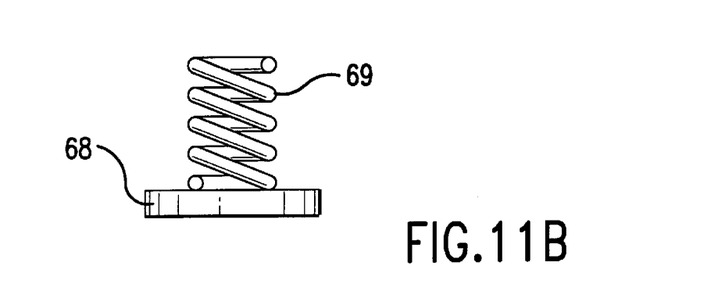

The sampler assembly 10 also preferably includes means by which the operator can view the collection process while doing so. As shown in FIGS. 4 and 9, the housing body 50 includes openings 56 spaced around its circumference. Preferably, six rectangular openings 56 are spaced around the housing body 50. However, any appropriate number of openings 56 may be used as long as at least on operator toed. Further, the openings 56 may be any shape that permits an operator to see through the opening 56.

Figure 3:
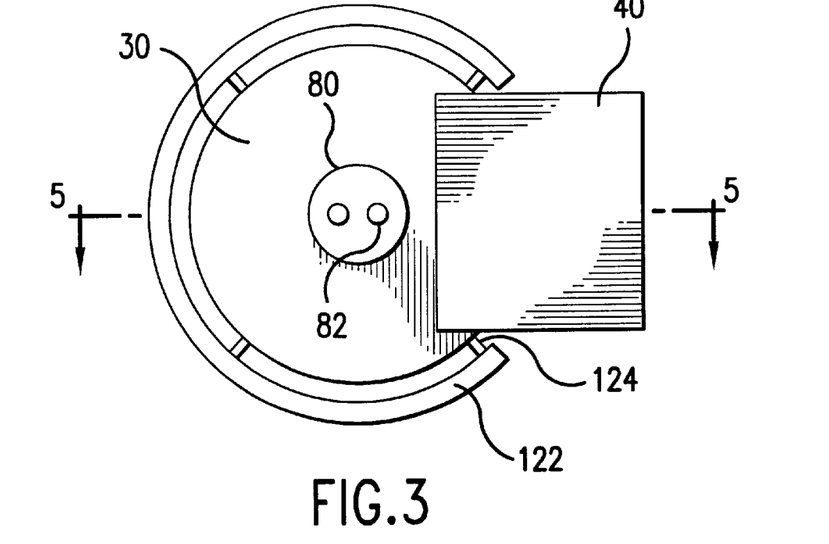
FIG. 3 is a top view of the sampler assembly along the line "3—3" in FIG. 2A.

A shield 120 is included to provide protection for the operator. Shield 120 encircles a portion of the housing body 50 as shown in FIGS. 2A, 3, and 4. The shield 120 may extend any desired angle around the housing 50 as long as the clearance required for any lateral adjustment device 60 is provided. The shield 120 is made of plexiglass or any other transparent material that can withstand a spray of the process. The operator may watch the sampling and when the collected sample reaches a desired level, the operator may close the valve 3 to stop the process flow through the supply line 12.

As shown in FIG. 5, shield supports 122 and brackets 124 are spaced along the outer surface of the housing body 50. Preferably, the shield supports 122 have the same curvature as the shield 120 and a similar length. Brackets 124 are spaced apart and support the shield supports 122. The shield 120 is connected to the shield supports 122 by screws or bolts. However, any appropriate connectors that can support the shield 120 may be used.

Preferably, the mounting bracket 40 is secured to the lid 30 by a weld. However, the connection could use bolts and screws which would allow easy disassembly of the lid 30 and bracket 40. The bracket 40 and the supporting structure 45 to which the bracket 40 is connected may be any material that can support the weight of the sampler assembly 10. Preferably, plug 80 is made from rubber. However, any material that can effectively seal the opening in the lid 30 may be used. While the connection between the lid 30 and the housing body 50 is threaded, any releasable connection may be used. Finally, as discussed above, the lid 30 and the housing body 50 are preferably of stainless steel, but can be any appropriate material.

The second preferred embodiment of a sampler assembly embodying the principles of the invention is shown in FIGS. 12A through 17 and described in detail below.

Similar to the first embodiment, the second preferred embodiment of the sampler assembly 110 includes two major subassemblies: a) a lid subassembly 114 coupled to the supply line 12 and to supporting structure 45; and b) a housing body subassembly 116 coupled to lid subassembly 114. Lid subassembly 114 includes: a lid 130 coupled to, and supported by, bracket 40; plug 80 disposed in lid 30; and supply line 12 and vent line 16 disposed in plug 80. Housing body subassembly 116 includes: an upper housing 150 releasably coupled to lid 130; a lower housing 160; lateral adjustment device 170; and axial adjustment device 70.

Some parts are the same between the two embodiments. Thus, some of the corresponding parts are not shown in FIGS. 12A through 17, which correspond to the second embodiment. For example, bracket 40, supporting structure 45, plug 80, supply line 12, and vent line 16 are a few of the corresponding parts. For most of these corresponding parts, the reference numbers are the same for both embodiments and in the following description.

The second embodiment of the sampler assembly 110 includes a housing body subassembly 116 with an upper housing 150 releasably coupleable to a lid 130. When upper housing 150 is coupled to lid 130, needles 14 and 18 are in communication with the interior of the upper housing 150. Similarly lateral and axial adjustment devices 170, 70 are used to provide support to a collection bottle in a lateral direction and axial direction, respectively. Lateral adjustment device 170 and axial adjustment device 70 ensure that a collection bottle remains in communication with the supply line 12 even if the sample being taken is at an extremely high pressure and high temperature.

Figure 12A:
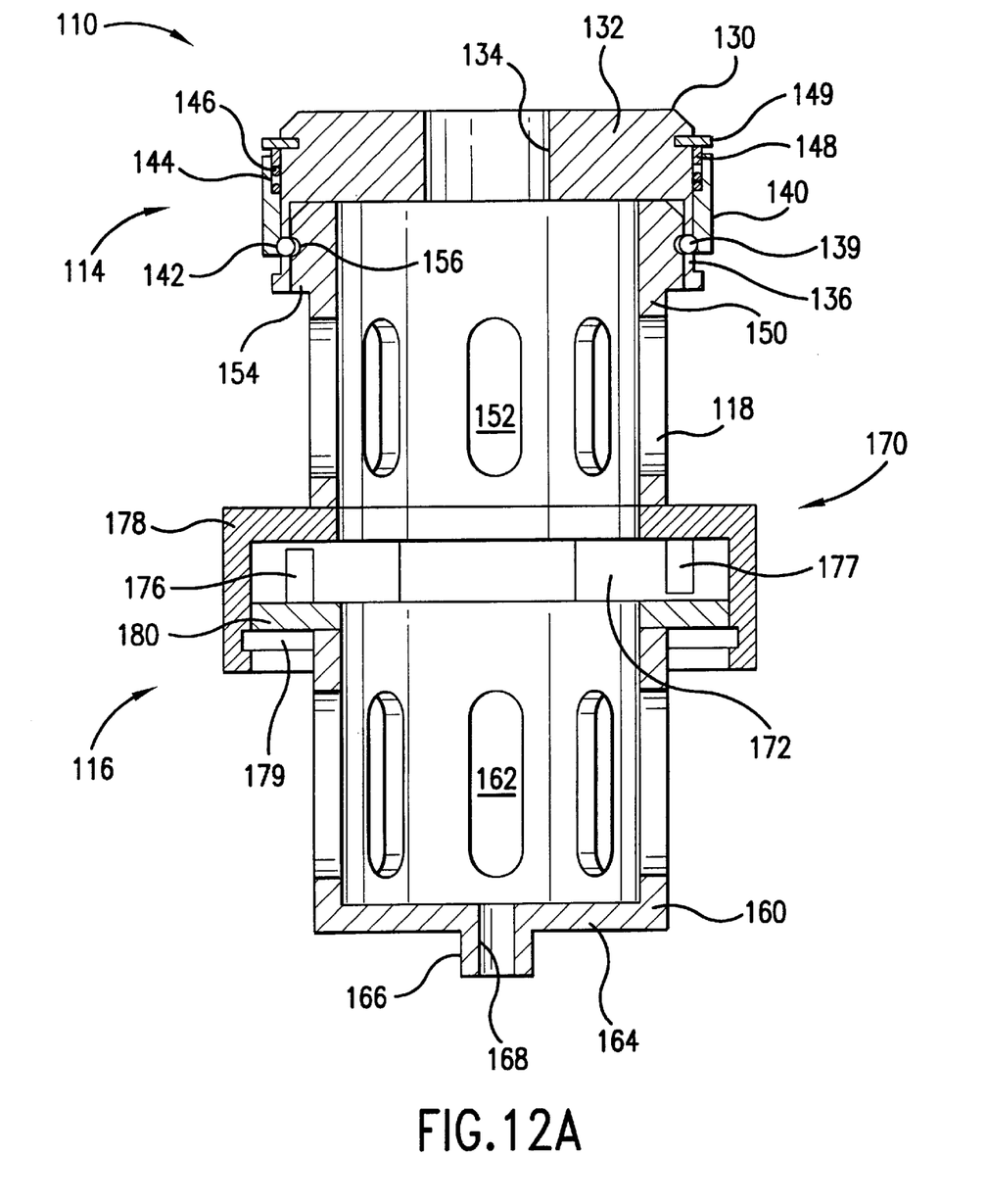
FIGS. 12A–12B are cross-sectional views of a second embodiment of a sampler assembly.
Figure 12B:
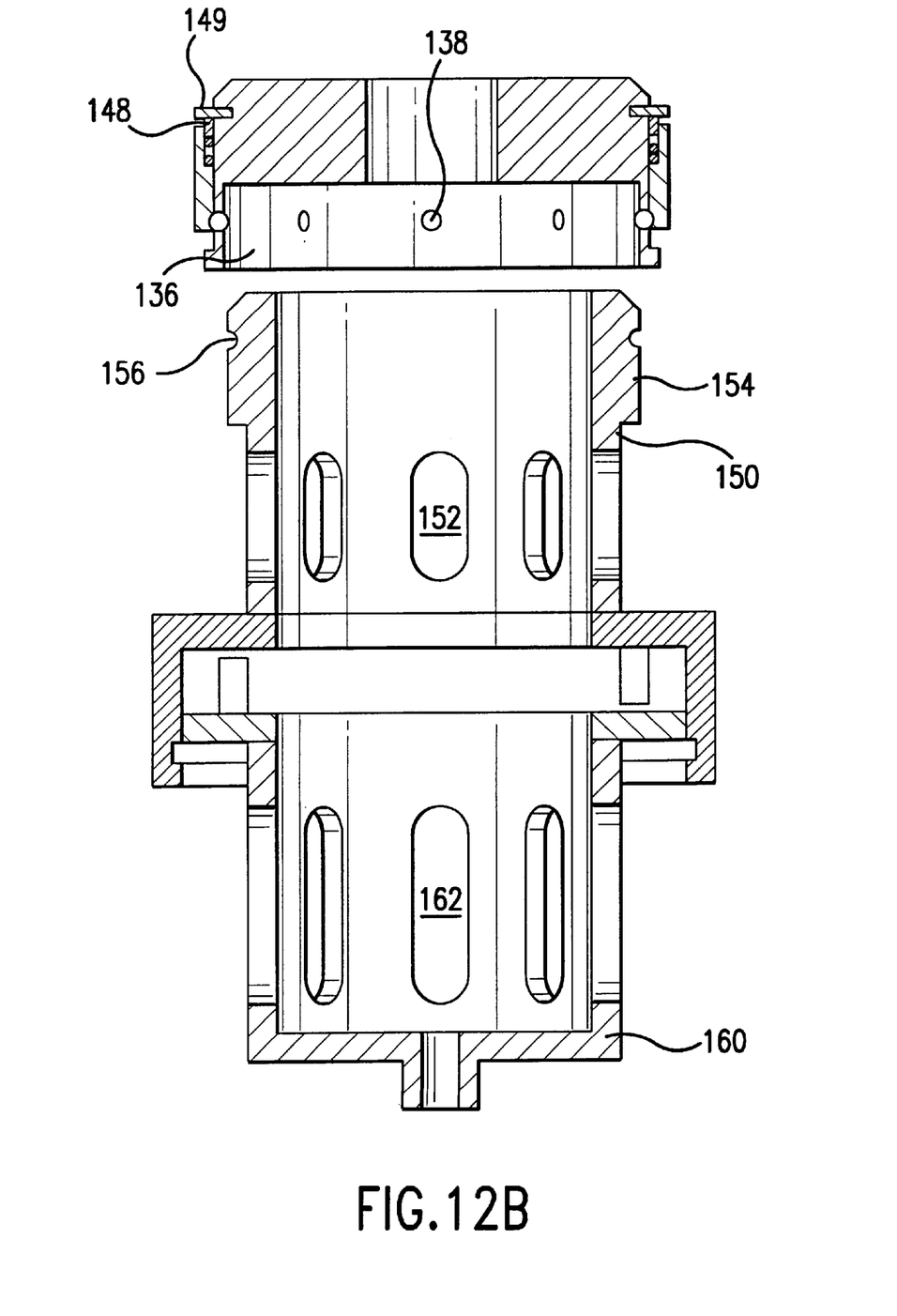
Figure 13A:
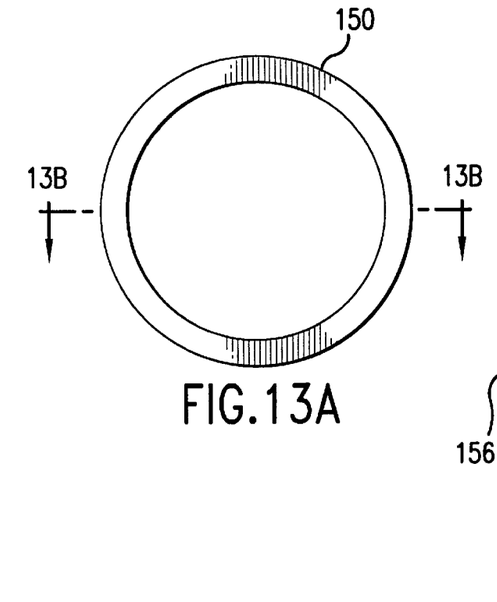
FIGS. 13A–13B are top and cross-sectional views of the upper housing of the sampler assembly of FIGS. 12A–12B.
Figure 13B:
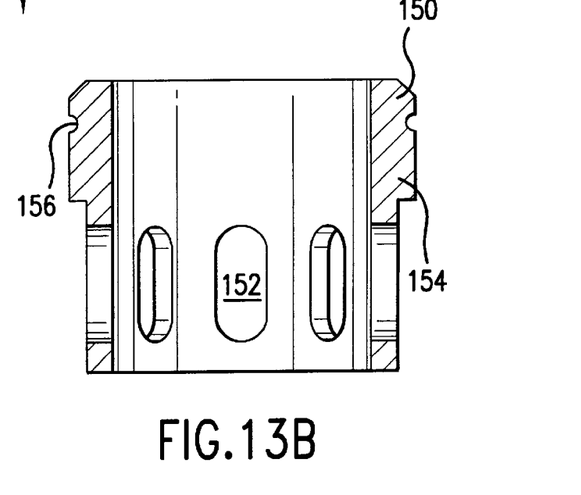
Figure 14A:
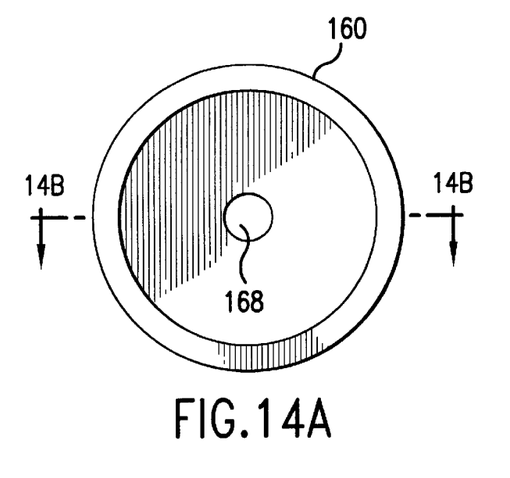
FIGS. 14A–14B are top and cross-sectional views of the lower housing of the sampler assembly of FIGS. 12A–12B.
Figure 14B:
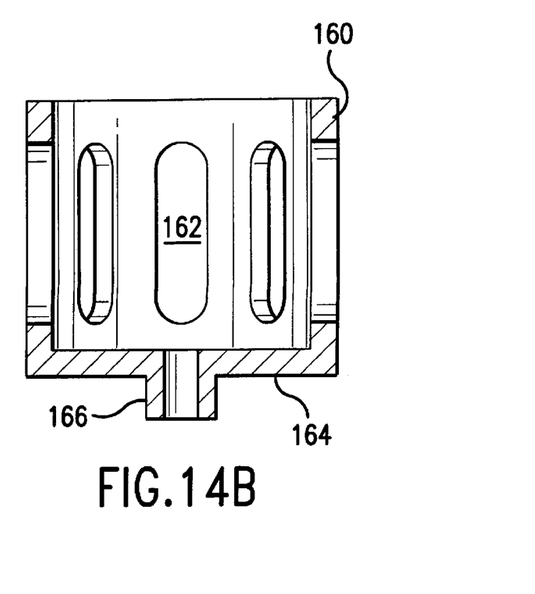
Figure 17:
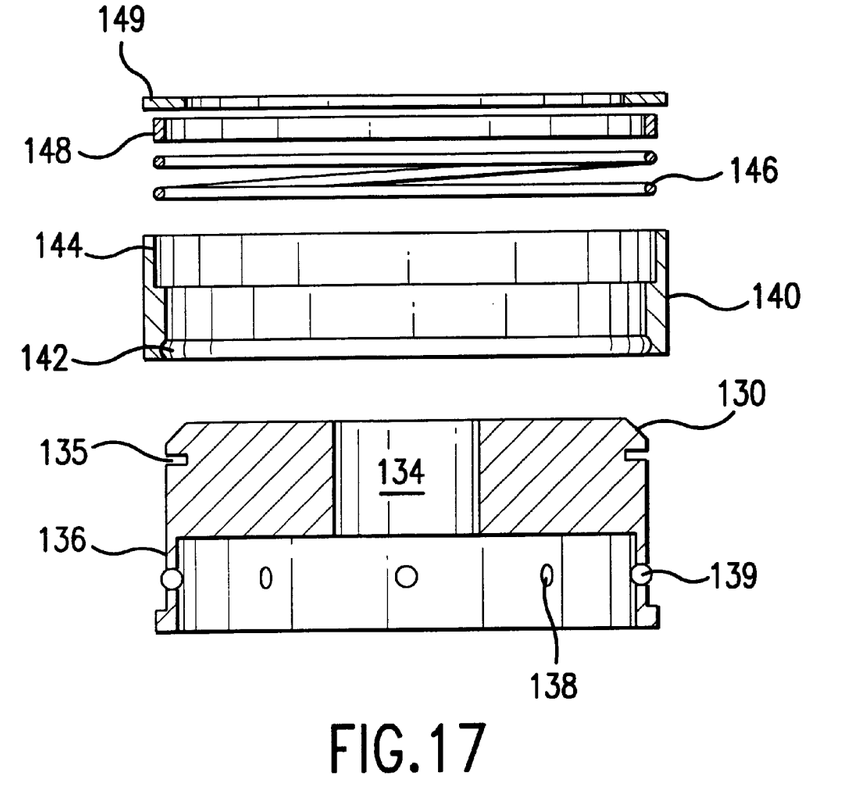
FIG. 17 is a cross-sectional view of the lid subassembly of the sampler assembly of FIGS. 12A–12B.

Turning to the connection between the lid 130 and the upper housing 150, the connection is shown in FIGS. 12A–12B and the lid 130 and its related components are shown in FIG. 17. Plug 80 is threaded into opening 134 in the body portion 132 of lid 130. Upper housing 150 is easily coupleable to the lid 130 to permit access to the inside of the upper housing 150. Once bracket 40 is secured to a supporting structure 45, the upper housing 150 is readily connected to and removed from the lid 130 by way of a ball/detent arrangement.

Upper housing 150 includes a ridge 154 near the top of the upper housing. The ridge 154 includes indentations 156 spaced equally around the ridge 154. As shown in FIGS. 12A and 17, the lid 130 has a side portion 136 with an inner surface having openings 138 therethrough. The openings 138 are spaced apart to be aligned with the indentations 156. Balls 139 are inserted into openings 138.

As the upper housing 150 is inserted into the lid 130, the balls 139 engage indentations 156. Coupling the upper housing 150 and the lid 130 involves the use of elements to retain the balls 139 in the openings 138 of the lid 130 as shown in FIGS. 12A and 17. Initially, a sleeve 140 is slid over the lid 130. Sleeve 140 includes indentations 142 that correspond to the openings 138 in the lid 130. Sleeve 140 also includes a flange 144 defining a cavity-like area into which a spring 146 is inserted. A tubular member 148 is then slid over the lid 130 to engage one end of the spring 146. The tubular member 148 and the spring are held in place by snap ring 149 which is slid onto lid 130 and engaged in groove 135 on the body portion 132 of the lid 130. The sleeve 140 and its related parts function to retain the balls 139 in place when the upper housing 150 is mounted to the lid 130.

The second embodiment includes a lateral adjustment device 170 that provides lateral support to a collection container. As shown in FIGS. 15A through 16B, the lateral adjustment device 170 includes fingers 172 that move either inwardly or outwardly as the lower housing 160 is rotated relative to the upper housing 150. The fingers 172 are moveable so that they contact the surface of the collection bottle 90.

Figure 15A:
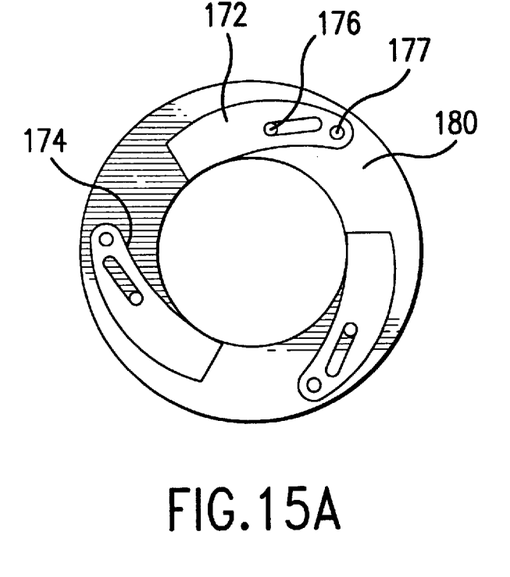
FIGS. 15A–15B are top views of the lateral adjustment device of the sampler assembly of FIGS. 12A–12B.
Figure 15B:
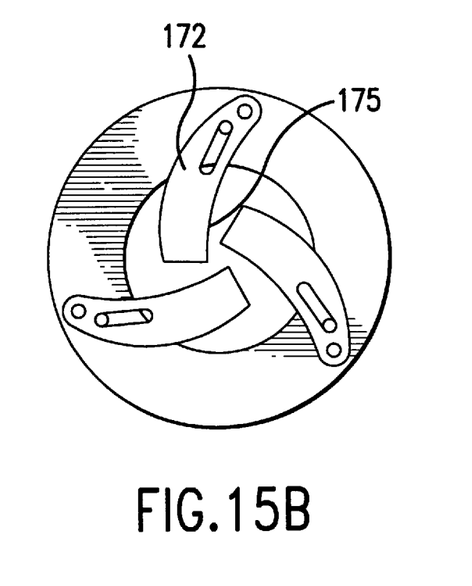
Figure 16A:
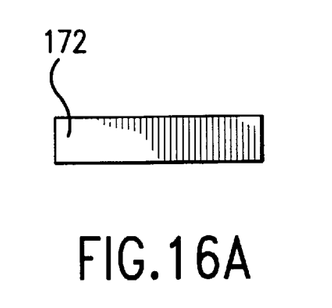
FIGS. 16A–16B are side and top views of the fingers of the sampler assembly of FIGS. 12A–12B.
Figure 16B:
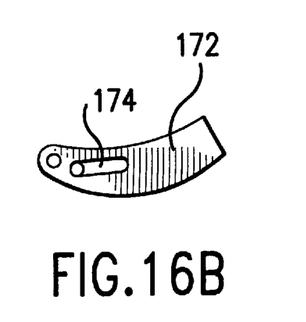

Preferably, each lateral adjustment device 170 includes three fingers 172 as shown in FIGS. 15A–15B. The fingers 172 move when the lower housing 160 rotates relative to the upper housing 150 after the upper housing 150 is mounted to the lid 130. To support a container, an operator rotates the lower housing 160 so that the fingers 172 engage the sides of a collection bottle 90. This arrangement facilitates the accommodation of different sizes of collection bottles.

Turning to the lateral adjustment device 170 in more detail, the upper housing 150 is coupled to a fixed member 178 by a weld. There are three pins 177 connected to the fixed member at spaced locations as shown in FIG. 15A. A finger 172 is mounted on each pin 177, thereby pivotally coupling each finger 172 to the fixed member 178.

Referring to FIGS. 12A–12B, the lower housing 160 is shown coupled to a rotating member 180 by a weld. A bearing member 179 is mounted in the fixed member 178. The bearing member 179 facilitates the rotation between the rotating member 180 and the fixed member 178, and therefore, between the upper housing 150 and lower housing 160. Preferably, the bearing member 179 is stainless steel.

In order to move, each finger 172 has to be connected to the rotating member 180 and the lower housing 160. Three pins 176 are connected to the rotating member 180 at spaced apart locations. As shown in FIGS. 15A–15B, each finger 172 includes a slot 174 into which a pin 176 is inserted. As the upper housing 150 and the lower housing 160 move relative to each other, each pin 176 moves along its corresponding slot 174. The movement of the pin 176 in the slot 174 forces the finger 172 to rotate about pin 177, and accordingly move inwardly or outwardly, depending on the direction of rotation.

The distance that the fingers 172 move inwardly is limited by the diameter of the collection container. If the fingers 172 engage the collection container and each pin 176 is not at an end of a slot 174, the friction between the pins 176 and the sides of the slots 174 will retain the fingers 172 in their current position. Preferably, the fingers are made of polytetrafluoroethylene (PTFE) so they do not scratch the surface of a collection bottle.

The housing body subassembly 116 includes an axial adjustment device 70 similar to that in the first embodiment of the sampler assembly. The axial adjustment device 70 is mounted to the bottom portion 164 of the lower housing 160 by way of mounting portion 166. The tube 74 is welded to the mounting portion 166 and the rod 72 is inserted through opening 168 and threaded into tube 74.

Although it is not shown in any of FIGS. 12A through 17, the second embodiment preferably includes a shield to protect an operator and equipment. The shield 120 may be mounted to fixed member 178 by bolts or other connectors that are strong enough to support the shield 120.

As shown in FIGS. 12A–12B, the upper housing 150 and the lower housing 160 include openings 152 and 162, respectively. Preferably, eight elongated openings are spaced around each housing. However, any appropriate number of openings may be used as long as at least one is provided. Further, the openings may be any shape that permits an operator to view the level of the sample.

Turning to the method of collecting a sample, a sampler assembly 10 having a collection bottle housing 20 is provided. Initially, the mounting bracket 40 is coupled to the lid 30 and then connected to a supporting structure 45. The plug 80 is threaded into opening 34 in the lid 30. The needles 14 and 18 of the supply line 12 and the vent line 16 are inserted into holes 82 of the plug 80.

When the housing body 50 is disconnected from the lid 30, a collection bottle 90 is inserted onto needles 14 and 18. The collection bottle 90 is pushed upwardly until the septum 92 contacts the bottom surface of the plug 80. Before the housing body 50 and the lid 30 are coupled, each manually adjusting component 60a is operated to move its pad 68 close to the inner surfaces of the housing body 50. Next, the housing body 50 is threaded onto the lid 30. As the housing 50 rotates, automatically adjusting components 60b contact the outer surface of the collection bottle 90. However, since the pads 68 are non-abrasive, the collection bottle 90 surface is not damaged.

After the housing body 50 is coupled to the lid 30, the lateral and axial adjustment devices 60, 70, are adjusted so that pads 68, 78, contact a surface of the collection bottle 90. As a result, the collection bottle 90 is supported on its sides and bottom surface.

At this time, the operator opens a valve 3 in the tap line 2 to permit the process to flow to the collection bottle 90. The operator may view the level of the collected sample through the shield 120 and openings 56 in the housing body 50. When the sample reaches the desired level in the collection bottle 90, the operator closes the valve 3 and the housing body 50 is disconnected from the lid 30. The collection bottle 90 may be removed from the needles 14 and 18 and subsequently analyzed.

The majority of the operation of the second embodiment is the same as that for the first embodiment. Mainly, only the connection of the upper housing 150 to the lid 130 and the adjustment of the lateral adjustment devices 170 are different. The upper housing 150 is coupled to the lid 130 and the lower housing 160 is coupled to the upper housing 150. Next, the lower housing 160 is rotated move the fingers 172 into engagement with the sides of the collection bottle 90. Also, the axial adjustment device 70 is adjusted so that pad 78 contacts a bottom surface of the collection bottle 90. As a result, the collection bottle 90 is supported on its sides and bottom surface. At this point the operator may proceed to collect a sample.

Although the disclosed embodiments includes separate lateral and axial adjustment devices, the artisan will recognize that is would be possible to use a single adjustment device that adjusts in a direction with both lateral and axial components. Thus, for example, a single adjustment device similar to the lateral adjustment device 60 could be mounted to advance in a direction diagonally upwardly and inwardly to engage the lower corner of the sample bottle, or even the side wall of the bottle provided that sufficient friction would be developed between the bottle sidewall and the adjustment device to support the weight of the bottle axially.

It is within the scope of the invention that the sampler assembly may be used by itself or with other sampler assemblies in parallel. If multiple sampler assemblies are used, a valve should be provided for each sampler assembly to control the process flow.

We claim:

1. A sampler assembly for collecting a sample of a material from a source of the material in either of a first collection bottle or a second collection bottle smaller than the first collection bottle, the sampler assembly comprising:
   a collection bottle housing;
   means coupleable to the source of material for establishing fluidic communication between the source of material and said housing;
   means coupled to said housing for selectively supporting within said housing each of the first and second collection bottles in operative association with said means for establishing fluidic communication, said means for selectively supporting the collection bottles including a lateral adjustment device that is adjustable in a lateral direction relative to the housing;

whereby either of the first and second collection bottles can be placed in said housing, and coupled to said means for establishing fluidic communication to collect the sample of material in the selected collection bottle from the source of material.

2. The sampler assembly of claim 1, wherein each of the collection bottles has a lateral dimension, the lateral dimension of the second collection bottle being smaller than the lateral dimension of the first collection bottle, and wherein said lateral adjustment device is adjusted in a lateral direction to engage and thereby support either of the first and second collection bottles.

3. The sampler assembly of claim 2, wherein said lateral adjustment device includes a first bottle engaging surface and means coupled to said first bottle engaging surface for manually adjusting the lateral position of said first bottle engaging surface with respect to said housing, whereby said first bottle engaging surface can be laterally positioned into engagement with either of the first or second collection bottles.

4. The sampler assembly of claim 3, wherein said laterally adjustable means further includes a second bottle-engaging surface and means mounted to said housing for laterally biasing said second bottle engaging surface toward said first bottle engaging surface.

5. The sampler assembly of claim 1, wherein each of the collection bottles has an axial dimension, the axial dimension of the second collection bottle being smaller than the axial dimension of the first collection bottle, and wherein said means for selectively supporting the collection bottles includes means adjustable in the axial direction to engage and thereby support either of the first and second collection bottles.

6. The sampler assembly of claim 5, wherein said axially adjustable means includes an axial bottle engaging surface and means coupled to said axial bottle engaging surface for manually adjusting the axial position of said axial bottle engaging surface with respect to said housing, whereby said axial bottle engaging surface can be axially positioned into engagement with either of the first or second collection bottles.

7. The sampler assembly of claim 1 wherein said sample bottle housing includes a lid portion and a body portion releasably coupleable to said lid portion.

8. The sampler assembly of claim 7 further including a mounting bracket secured to one of said lid portion and said body portion and securable to a supporting structure to support said sampler assembly.

9. The sampler assembly of claim 1 wherein said housing includes an aperture through which a collection bottle disposed in said housing can be viewed and further including a substantially transparent shield mounted to said housing adjacent said opening, whereby an operator of the sampler assembly can view the collection bottle during filling with a sample and is protected by said shield from the sample.

10. The sampler assembly of claim 2, wherein said laterally adjustable means includes fingers and means coupled to said fingers for manually adjusting the lateral position of said fingers with respect to said housing, whereby said fingers can be laterally positioned into engagement with either of the first or second collection bottles.

11. The sampler assembly of claim 2, wherein said sample bottle housing includes an upper housing and a lower housing coupled together.

12. The sampler assembly of claim 11, wherein said lower housing is rotatable relative to said upper housing.

13. The sampler assembly of claim 12, wherein said laterally adjustable means includes fingers and means coupled to said fingers for manually adjusting the lateral position of said fingers with respect to said collection bottle housing, whereby said fingers can be laterally positioned into engagement with either of the first or second collection bottles when said lower housing is rotated relative to the upper housing.

14. A method of collecting a sample of a desired quantity of a material from a source of the material, the method comprising the steps of:

disposing adjacent the source of material a sampler assembly having a collection bottle housing, means coupleable to the source of material for establishing fluidic communication between the source of material and the housing, and means coupled to the housing for selectively supporting within the housing each of a first and a second collection bottle in operative association with the means for establishing fluidic communication, said support means including means adjustable in the lateral direction to engage and thereby support either of the first and the second collection bottles;

selecting one of the first collection bottle or the second collection bottle, the second collection bottle having a capacity and having dimensions smaller than those of the first collection bottle including a lateral dimension of the second collection bottle being smaller than a lateral dimension of the first collection bottle, the selected bottle being selected to accommodate the desired quantity of material;

disposing the selected collection bottle within the housing in operative association with the means for establishing fluidic communication; and adjusting the support means to support the selected collection bottle including adjusting the laterally adjustable means to engage a side wall of, and thereby support, the selected collection bottle.

15. The method of claim 14, wherein the first collection bottle has an axial dimension greater than an axial dimension of the second collection bottle, the support means includes means adjustable in the axial direction to engage and thereby support either of the first and second collection bottles, and said adjusting step includes adjusting the axially adjustable means to engage a lower end of, and thereby support, the selected collection bottle.

* * * * *